US010265248B2

(12) United States Patent
Kadobayashi et al.

(10) Patent No.: US 10,265,248 B2
(45) Date of Patent: *Apr. 23, 2019

(54) COMPOSITE MATERIAL HAVING REDUCED DEGRADATION OF PASTY PROPERTY

(71) Applicant: SHOFU INC., Kyoto (JP)

(72) Inventors: Yusei Kadobayashi, Kyoto (JP); Masako Shigezawa, Kyoto (JP)

(73) Assignee: SHOFU INC., Kyoto (JP)

( * ) Notice: Subject to any disclaimer, the term of this patent is extended or adjusted under 35 U.S.C. 154(b) by 316 days.

This patent is subject to a terminal disclaimer.

(21) Appl. No.: 14/797,538

(22) Filed: Jul. 13, 2015

(65) Prior Publication Data
US 2016/0030298 A1 Feb. 4, 2016

(30) Foreign Application Priority Data

Jul. 29, 2014 (JP) .................................. 2014-154177

(51) Int. Cl.
A61K 6/08 (2006.01)
A61K 6/083 (2006.01)
A61K 6/00 (2006.01)

(52) U.S. Cl.
CPC ............ A61K 6/083 (2013.01); A61K 6/0047 (2013.01); A61K 6/0091 (2013.01)

(58) Field of Classification Search
CPC ....... A61K 6/0047; A61K 6/083; A61K 6/091
See application file for complete search history.

(56) References Cited

U.S. PATENT DOCUMENTS

| 4,010,545 | A | 3/1977 | Kilian et al. |
| 6,620,861 | B1* | 9/2003 | Nakatuka ............ A61K 6/0008 523/115 |
| 9,603,779 | B2* | 3/2017 | Kadobayashi ........... A61K 6/02 |
| 2003/0036582 | A1 | 2/2003 | Yamakawa et al. |
| 2003/0181541 | A1 | 9/2003 | Wu et al. |
| 2009/0048366 | A1 | 2/2009 | Torii et al. |
| 2009/0076182 | A1 | 3/2009 | Tanaka et al. |
| 2010/0010115 | A1 | 1/2010 | Kohro et al. |

FOREIGN PATENT DOCUMENTS

| EP | 0 988 851 | 3/2000 |
| EP | 2 279 723 | 2/2011 |
| JP | 8-143747 | 6/1996 |
| JP | 9-194674 | 7/1997 |
| JP | H09-194674 A | 7/1997 |
| JP | 2009-67746 | 4/2009 |
| JP | 2009-120849 | 6/2009 |
| JP | 2010-18524 | 1/2010 |
| JP | 2012-153640 | 8/2012 |
| WO | 2007/088628 | 8/2007 |
| WO | 2016/017581 | 2/2016 |
| WO | 2016/017582 | 2/2016 |

OTHER PUBLICATIONS

Extended European Search Report dated Apr. 1, 2016 in corresponding European patent application No. 15176498.2.

* cited by examiner

Primary Examiner — Sanza L. McClendon
(74) Attorney, Agent, or Firm — Wenderoth, Lind & Ponack, L.L.P.

(57) ABSTRACT

A composite material including silanated filler and mixed polymerizable monomer, having a stable pasty property which keeps well and has a consistent usability. A composite material containing a silanated filler, a polymerizable monomer, and a polymerization initiator, and may be produced by a process which includes in order of a mixed polymerizable monomer preparing step, a mixed polymerizable monomer preserving step, a composite material preparing step, a composite material preserving step, a composite material filling step, and a small quantity preserving container preserving step.

4 Claims, 4 Drawing Sheets

Fig. 1

Table 1
Preparing condition, mixing condition, preserving condition and evaluation result of mixed polymerizable monomer

| | | | Sample1 | Sample2 | Sample3 | Sample4 | Sample5 | Sample6 |
|---|---|---|---|---|---|---|---|---|
| Mixed polymerizable monomer | Polymerizable Monomer | Bis-GMA(%) | 50 | Same as Sample 1 | 55 | Same as Sample 1 | Same as Sample 1 | Same as Sample 1 |
| | | UDMA(%) | 25 | | 20 | | | |
| | | TEGDM(%) | 5 | | 5 | | | |
| | | 3G(%) | 4 | | 4 | | | |
| | | HEMA(%) | 3 | | 3 | | | |
| | Polymerizable Monomer Bearing Phosphate Ester Group | 2-MEP(%) | 2 | | 2 | | | |
| | | Bis-MEP(%) | 0 | | 0 | | | |
| | | 6-MHPA(%) | 1 | | 1 | | | |
| | | 4-AET(%) | 2 | | 0 | | | |
| | Polymerizable Monomer bearing Dibasic Acid Carboxyl Group | 4-MET(%) | 0 | | 2 | | | |
| | | BBA-Na(%) | 5 | | 0 | | | |
| | Polymerization accelerator | ER(%) | 0 | | 3 | | | |
| | | OTT(%) | 1 | | 1 | | | |
| | Polymerization Initiator | CQ(%) | 2 | | 2 | | | |
| | Polymerization inhibitor | BHT (pts.wt.) | 0.1 | | 0.1 | | | |
| | Total | | 100.1 | | 100.1 | | | |
| Mixing condition | mixing machine | BM, TM | BM | BM | BM | TM | BM | TM |
| | mixing condition | Mixing temperature(°C) | 5 | 30 | 5 | 55 | -5 | 55 |
| | | Mixing period (hour) | 0.25 | 9 | (5minutes) | 22 | (5minutes) | 30 |
| Preserving condition | mixed polymerizable monomer | Preserving period (day) | 30 | 365 | 10 | 400 | 0 | 600 |
| | | Preserving temperature(°C) | 5 | 5 | 5 | 25 | -5 | 40 |
| Result | Viscous test | (mPa·s) | 8630 | 8520 | 7530 | 7420 | 6930 | 7200 |
| | | evaluation | A | A | A | A | B | A |
| | Transmittance | % | 97% | 97% | 97% | 97% | 97% | 97% |
| | Hardening test | (kgf/m²) | 15.2 | 15.2 | 15.7 | 15.7 | 15.2 | 15.2 |

BM:mixer (Aikosha Inc.)(which use blade for mixing, TM:tumbler mixer (Seiwa Giken Inc.)

Fig.2

Table 2
Preparing condition, mixing condition, preserving condition and evaluation result of composite material

| | | | Example1 | Example2 | Example3 | Example4 | Example5 | Example6 | Example7 | Example8 | Comparative Example1 | Comparative Example2 |
|---|---|---|---|---|---|---|---|---|---|---|---|---|
| Composite material | Mixed polymerizable monomer | Sample type | 1 | 2 | 1 | 2 | 3 | 4 | 3 | 4 | 5 | 6 |
| | | (g) | 2000 | 2000 | | | | | | | 2000 | 2000 |
| | Filter | ASG filter (g) | 1400 | 1400 | | | | | | | 1400 | 1400 |
| | | FASG filter (g) | | | | | | | | | | |
| | | Silane treatment liquid | a | b | | | | | | | a | b |
| | | Preservation period after silane treatment (day) | 50 | 500 | | | | | | | 0 | 700 |
| | Ultrafine particle filter | R-972(g) | 60 | 60 | | | | | | | 60 | 60 |
| Mixing condition | Mixing machine | NJ, PM | PM | PM | Same as Example 1 | Same as Example 2 | Same as Example 1 | Same as Example 2 | Same as Example 1 | Same as Example 2 | PM | PM |
| | Ultrafine particle filter mixing condition | Mixing temperature(°C) | 3 | 60 | | | | | | | 5 | 60 |
| | | Mixing period (minute) | 5 | 30 | | | | | | | 5 | 30 |
| | | Mixing temperature(°C) | 5 | 60 | | | | | | | 5 | 60 |
| | | Mixing period (minute) | 5 | 30 | | | | | | | 5 | 30 |
| | Ultrafine particle filter defoaming condition | Pressure reduce condition (Torr) | 5 | 150 | | | | | | | 5 | 150 |
| | Filter mixing condition | Mixing temperature(°C) | 5 | 60 | | | | | | | 5 | 60 |
| | | Mixing period (minute) | 5 | 40 | | | | | | | 5 | 40 |
| | | Mixing temperature(°C) | 5 | 60 | | | | | | | 5 | 60 |
| | | Mixing period (minute) | 5 | 30 | | | | | | | 5 | 30 |
| | Filter defoaming condition | Pressure reduce condition (Torr) | 5 | 150 | | | | | | | 5 | 150 |
| Large amount preserving condition | | Preserving period(day) | 30 | 365 | 10 | 500 | 30 | 365 | 10 | 500 | 1 | 1 |
| | | Preserving temperature(°C) | 1 | 8 | 1 | 23 | 1 | 8 | 1 | 23 | -3 | 30 |
| Large amount evaluation result | Hardening test | (kg/cm) | 46.3 | 35.2 | 45.9 | 35.6 | 46.2 | 45.9 | 46.1 | 45.8 | 45.7 | 45.6 |
| | Property/visual test | evaluation | A | A | B | B | A | A | C | C | D | D |
| Small amount preserving condition | | Filling temperature(°C) | 15 | 45 | 15 | 45 | 15 | 45 | 15 | 45 | 10 | 60 |
| | | Preserving period(day) | 50 | 2000 | 100 | 1000 | 50 | 2000 | 100 | 1000 | 1 | 2500 |
| | | Preserving temperature(°C) | 3 | 23 | 3 | 35 | 3 | 23 | 3 | 35 | -3 | 40 |
| Small amount evaluation result | property visual test | evaluation | A | A | B | A | B | B | C | B | D | D |
| | Evaluation of property variation between lot | evaluation | B | B | C | C | C | C | C | C | D | D |
| | Evaluation of property variation in syringe | evaluation | B | B | C | C | B | B | C | C | D | D |
| | Bubbles mixing test | evaluation | B | B | B | B | B | B | B | B | D | D |
| | Fluidity (flow) test area( mm²) | Immediately after filling | 1311.24 | 1554.50 | 1274.91 | 1526.68 | 1281.25 | 1485.42 | 1423.59 | 1675.54 | 1151.51 | 1675.54 |
| | | 60 days after | 1145.50 | 1281.25 | 1017.36 | 1249.73 | 1068.86 | 1249.73 | 1218.60 | 1437.99 | 994.88 | 1492.25 |
| | | 120 days after | 1074.67 | 1206.26 | 950.67 | 1151.31 | 983.73 | 1151.31 | 1127.58 | 1338.97 | 803.84 | 1256.00 |
| | | 3 years after | 1068.86 | 1200.12 | 939.77 | 1139.81 | 972.65 | 1139.81 | 1115.71 | 1326.03 | 660.19 | 1074.67 |
| | | 5 years after | 1040.09 | 1175.69 | 912.81 | 1115.71 | 923.54 | 1098.03 | 1068.86 | 1281.25 | 506.43 | 865.26 |
| | | 6 years after | 854.87 | 989.30 | 730.25 | 934.35 | 749.53 | 902.13 | 880.97 | 1068.86 | 379.94 | 781.80 |
| | Intermittency extrusion test | evaluation | A | A | A | A | A | A | A | A | A | A |

BM:mixer (Aikosha Inc.)which use blade for mixing, TM:tumbler mixer (Seiwa Giken Inc.)

Fig.3

Table 3
Preparing condition, mixing condition, preserving condition and evaluation result of composite material

| | | | Example9 | Example10 | Example11 | Example12 | Example13 | Example14 | Example15 | Example16 | Comparative Example3 | Comparative Example4 |
|---|---|---|---|---|---|---|---|---|---|---|---|---|
| Composite material | Mixed polymerizable monomer | Sample type | 1 | 2 | 1 | 2 | 3 | 4 | 3 | 4 | 5 | 6 |
| | | (g) | 2000 | 2000 | | | | | | | 2000 | 2000 |
| | Filter | ASi filler (g) | 7000 | 7000 | | | | | | | 7000 | 7000 |
| | | FASG filler (g) | | | | | | | | | | |
| | | Silane treatment liquid | a | b | | | | | | | a | b |
| | | Preservation period after silane treatment (day) | 30 | 500 | | | | | | | 0 | 700 |
| | Ultrafine particle filler | R 972 (g) | 30 | 30 | | | | | | | 30 | 30 |
| | | ND, PM | ND | ND | | | | | | | ND | ND |
| Mixing condition | Mixing machine | | | | Same as Example 9 | Same as Example 10 | Same as Example 9 | Same as Example 10 | Same as Example 9 | Same as Example 10 | | |
| | Ultrafine particle filler mixing condition | Mixing temperature(°C) | 5 | 60 | | | | | | | 5 | 60 |
| | | Mixing period (minute) | 5 | 30 | | | | | | | 5 | 30 |
| | Ultrafine particle filler defoaming condition | Mixing temperature(°C) | 5 | 60 | | | | | | | 5 | 60 |
| | | Mixing period (minute) | 5 | 30 | | | | | | | 5 | 30 |
| | | Pressure reduce condition (Torr) | 5 | 150 | | | | | | | 5 | 150 |
| | Filter mixing condition | Mixing temperature(°C) | 5 | 60 | | | | | | | 5 | 60 |
| | | Mixing period (minute) | 5 | 40 | | | | | | | 5 | 40 |
| | Filter defoaming condition | Mixing temperature(°C) | 5 | 60 | | | | | | | 5 | 60 |
| | | Mixing period (minute) | 5 | 30 | | | | | | | 5 | 30 |
| | | Pressure reduce condition (Torr) | 5 | 150 | | | | | | | 5 | 150 |
| Large amount preserving condition | | Preserving period(day) | 30 | 365 | 10 | 500 | 30 | 365 | 10 | 500 | 1 | 1 |
| | | Preserving temperature(°C) | 1 | 8 | 8 | 23 | 1 | 8 | 1 | 23 | 1 | 30 |
| Large amount evaluation result | Hardening test | (kgf/m²) | 52.4 | 53.4 | 53.5 | 52.1 | 55.4 | 53.7 | 52.9 | 51.6 | 53.2 | 52.6 |
| | Property-visual test | evaluation | A | A | B | A | A | A | C | C | D | D |
| Small amount condition | Small amount preserving container | Filling temperature(°C) | 15 | 45 | 15 | 45 | 15 | 45 | 15 | 45 | 10 | 60 |
| | | Preserving period(day) | 50 | 2000 | 100 | 1000 | 50 | 2000 | 100 | 1000 | 1 | 2500 |
| | | Preserving temperature(°C) | 3 | 23 | 3 | 35 | 3 | 23 | 3 | 35 | 3 | 40 |
| Small amount evaluation result | property visual test | evaluation | B | B | B | B | B | B | B | B | D | D |
| | Evaluation of property variation between lots | evaluation | A | B | C | B | C | C | C | C | D | D |
| | Evaluation of property variation in section | evaluation | B | B | C | C | B | C | C | C | D | D |
| | Bubbles mixing test | evaluation | B | B | B | B | B | B | B | B | D | D |
| | Fluidity(flow nest area, mm²) | Immediately after filling | 356.15 | 329.96 | 408.07 | 359.50 | 292.40 | 365.57 | 390.37 | 390.37 | 262.89 | 333.12 |
| | | 60 days after | 229.54 | 211.13 | 268.67 | 232.23 | 195.97 | 251.52 | 266.38 | 280.41 | 191.04 | 254.34 |
| | | 120 days after | 198.66 | 182.67 | 234.94 | 193.44 | 160.52 | 210.57 | 243.16 | 237.67 | 132.67 | 191.37 |
| | | 3 years after | 198.46 | 191.37 | 232.23 | 191.04 | 158.29 | 208.37 | 240.41 | 234.94 | 86.55 | 126.61 |
| | | 5 years after | 186.17 | 171.95 | 218.93 | 181.37 | 138.86 | 191.04 | 218.93 | 216.31 | 52.78 | 84.91 |
| | | 6 years after | 111.16 | 102.02 | 143.07 | 109.36 | 75.39 | 114.93 | 138.86 | 140.95 | 27.53 | 51.50 |
| | Intermittency extrusion test | evaluation | A | A | B | A | A | A | B | A | C | C |

BM mixer (Aikosha Inc.,)which use blade for mixing. TM:tumbler mixer (Seiwa Giken Inc.)

Fig.4

Table 4
Fluidity (flow) test result and difference between present time and last time at small amount preservation container preservation

| mm²(difference between present time and last time) | Example1 | Example2 | Example3 | Example4 | Example5 | Example6 | Example7 | Example8 | Comparative Example1 | Comparative Example2 |
|---|---|---|---|---|---|---|---|---|---|---|
| 60 days after | 265.74 | 273.25 | 257.55 | 276.95 | 212.38 | 235.69 | 205.98 | 237.54 | 156.63 | 183.38 |
| 120 days after | 70.84 | 74.98 | 66.69 | 98.22 | 85.13 | 98.22 | 91.02 | 99.03 | 101.04 | 236.23 |
| 3 years after | 5.80 | 6.15 | 10.90 | 11.99 | 11.08 | 11.99 | 11.87 | 12.94 | 143.66 | 181.34 |
| 5 years after | 28.77 | 24.43 | 26.96 | 23.80 | 49.10 | 41.49 | 46.83 | 44.78 | 153.73 | 209.41 |
| 6 years after | 185.23 | 186.39 | 182.56 | 181.37 | 174.02 | 195.80 | 187.90 | 212.38 | 126.51 | 163.46 |

| mm²(difference between present time and last time) | Example9 | Example10 | Example11 | Example12 | Example13 | Example14 | Example15 | Example16 | Comparative Example3 | Comparative Example4 |
|---|---|---|---|---|---|---|---|---|---|---|
| 60 days after | 126.60 | 118.76 | 139.41 | 127.26 | 96.44 | 111.34 | 104.00 | 109.96 | 71.83 | 78.78 |
| 120 days after | 30.89 | 28.47 | 33.72 | 38.89 | 35.44 | 40.96 | 43.21 | 42.74 | 58.37 | 72.97 |
| 3 years after | 0.29 | 1.30 | 2.71 | 2.40 | 2.24 | 2.60 | 2.76 | 2.72 | 46.12 | 54.75 |
| 5 years after | 12.29 | 9.42 | 13.31 | 9.67 | 19.43 | 17.53 | 21.48 | 18.63 | 33.76 | 41.71 |
| 6 years after | 75.01 | 69.93 | 75.86 | 72.06 | 63.47 | 76.11 | 80.07 | 75.36 | 25.46 | 33.40 |

COMPOSITE MATERIAL HAVING REDUCED DEGRADATION OF PASTY PROPERTY

BACKGROUND

The present disclosure relates to a dental composite material used for a filling restoration, a prosthetic restoration, a temporary sealing, a temporary adhering, a prosthesis preparation, an adhesion, a cementation, a crypt fissure sealing in the dental field, more specifically, relates to a pasty composite material prepared by mixing a silanated filler and a polymerizable monomer, which is used for a composite resin (including for a facing crown and for a restoration or the like), a temporary sealing material, a temporary adhering material, a resin cement, an adhesive, a fissure sealant.

In the dental field, a composite material is prepared by mixing a silanated filler and a polymerizable monomer in the form of a paste. The pasty composite material (the composite material in the form of a paste) is provided to dentists and dental technicians, which are the user of the composite material, in a packaging container filled with the composite material. Although the composite material may be blended with an adhesive monomer, a pigment, or the like, in accordance with the purpose of use, the composite material is generally prepared in the form of a paste by mixing a silanated filler and a polymerizable monomer in the appropriate amount, and then is filled in a packaging container.

It is difficult to stabilize a pasty property of the pasty composite material. For example, in the case where the composite material is filled in a syringe container, the pasty property of the pasty composite material at an initial stage of discharging from the syringe container is different from that at an end stage of discharging from the syringe container. Also, the pasty property of the pasty composite material immediately after production is different from that of the pasty composite material preserved for a predetermined period.

The property of the composite material in which the pasty property is not stable significantly varies according to the packaging container used to package the composite material.

It is known that the pasty property and quality of the pasty composite material vary according to a mixing method or a mixing process in a paste production method. However, it has not been known that the composite material having a stable pasty property is obtained by a specific mixing procedure or a specific mixing method.

In a conventional paste, bubbles caused by the mixing and/or a variation of a pasty property occur to cause non-uniform polymerization and the quality of final products varies greatly because of a large variation of a flow value after preparation.

A consistent usability is required in a dental composite material by dentists and dental technicians.

BRIEF SUMMARY

Dentists and dental technicians are requesting a composite material having a stably pasty property. The stably pasty property of a composite material is to keep a good and consistent usability.

The disclosure provides a composite material having a stably pasty property, especially provides a dental composite material that dentists and dental technicians may use stably. For example, the method described herein provides a stable the composite material.

To keep a stably pasty property has been required for a pasty composite material if the composite material is filled in various syringe containers that are different in form.

To obtain a consistent pasty property from an initial period to a later period in discharging from a syringe container has been required for a pasty composite material filled in a syringe container. To obtain a consistent pasty property from immediately after manufacturing to after preserving for a certain period of time has been required for a pasty composite material.

It was impossible to obtain a pasty property that is the same at all times in a composite material discharged from a syringe container.

A composite material discharged from a syringe container includes unevenness and it was impossible to keep a stable pasty property.

A pasty property of a composite material filled in a syringe container changes according to a method of use including a continuous use, an intermittent use, and the case that an unused term exists etc., it was impossible to keep a stable pasty property.

A pasty property of a composite material changes according to a syringe container in which the composite material is filled. To obtain a stable pasty property has been required for a pasty composite material when each composite material is filled in different container.

The bubbles caused by mixing were observed in a composite material filled in a syringe container. Therefore, it has been necessary to perform additional work to removing the bubbles to a packaging process where the composite material is filled in a syringe container.

Generally, an inspection process has been included in a process of manufacturing a composite material. However, an appropriate time for performing a inspection process for preparing stable a pasty composite material has not been known. Further, in order to prepare a stable composite material, it has been important to find an appropriate time for performing the inspection process. The embodiments described herein can prepare a composite material having a stable pasty property by using an appropriate time for performing an appropriate inspection process in a manufacturing process.

BRIEF DESCRIPTION OF THE DRAWINGS

A more complete appreciation of the present invention and many of the attendant advantages thereof will be readily obtained as the same becomes better understood by reference to the following detailed description when considered in connection with the accompanying drawings, wherein:

FIG. 1 is preparing condition, mixing condition, preserving condition and evaluation result of mixed polymerizable monomer;

FIG. 2 is preparing condition, mixing condition, preserving condition and evaluation result of composite material FIG. 3 is Preparing condition, mixing condition, preserving condition and evaluation result of composite material; and FIG. 4 is fluidity (flow) test result and difference between present and last time at small amount preservation container preservation.

DETAILED DESCRIPTION

Described herein is a composite material containing a silanated filler, a polymerizable monomer, and a polymerization initiator, and the composite material is produced by a process that comprises in order of: a mixed polymerizable monomer preparing step that includes a step of mixing a polymerizable monomer and a polymerization initiator to prepare a mixed polymerizable monomer, a mixed polymerizable monomer preserving step that includes a step of preserving the mixed polymerizable monomer in a mixed polymerizable monomer preserving container, a composite material preparing step that includes a step of mixing the mixed polymerizable monomer and a silanated filler to prepare a composite material, a composite material preserving step that includes a step of preserving the composite material in a composite material preserving container, a composite material filling step that includes a step of filling the composite material into a small quantity preserving container, a small quantity preserving container preserving step that includes a step of preserving the composite material in the small quantity preserving container.

Also described herein is a composite material containing a silanated filler, a polymerizable monomer, and a polymerization initiator, and is produced by a process that comprises in order of: a mixed polymerizable monomer preparing step that includes a step of mixing a polymerizable monomer and a polymerization initiator to prepare a mixed polymerizable monomer, a composite material preparing step that includes a step of mixing the mixed polymerizable monomer and a silanated filler to prepare a composite material, a composite material filling step that includes a step of filling the composite material into a small quantity preserving container, a small quantity preserving container preserving step that includes a step of preserving the composite material in the small quantity preserving container, wherein; the composite material preparing step includes a step of performing in order of a particulate filler kneading step, a defoaming step after kneading the particulate filler, a silanated filler kneading step, and a defoaming step after kneading the silanated filler.

The mixed polymerizable monomer preserving step preferably includes a mixed polymerizable monomer evaluation step. Performing the mixed polymerizable monomer evaluation step in the mixed polymerizable monomer preserving step contributes a stable supply of the composite material.

Also, the composite material preserving step preferably includes a composite material evaluation step. Performing the composite material evaluation step in the composite material preserving step contributes to a stable production of the composite material.

Further, the small quantity preserving container is preferably a syringe container. The composite material becomes stable by preserving in a predetermined period in the syringe container, which is a container used by an end user.

The present disclosure also provides for a composite material containing a silanated filler, a polymerizable monomer, and a polymerization initiator, and is produced by a process which comprises in order of a mixed polymerizable monomer preparing step, a mixed polymerizable monomer preserving step, a composite material preparing step, a composite material preserving step, a composite material filling step, and a small quantity preserving container preserving step.

The mixed polymerizable monomer preparing step includes a step of charging a polymerization initiator into a polymerizable monomer in a mixing container, and mixing the polymerizable monomer and the polymerization initiator at a mixing temperature of 1-60° C. for a mixing period of 1 minute-24 hours to prepare a mixed polymerizable monomer.

The mixed polymerizable monomer preserving step includes a step of preserving 1-50 liters of mixed polymerizable monomer prepared in the mixed polymerizable monomer preparing step at preserving temperature of 1-23° C. for a preserving period of 10 days-1.5 years.

The composite material preparing step includes a step of performing a kneading step, and a defoaming step, at the ratio of 0.1-9 parts by weight of the silanated filler based on 1 part by weight the mixed polymerizable monomer, which includes a step of charging the silanated filler into the mixed polymerizable monomer.

When the composite material contains particulate filler, the material preparing step includes a step of performing in order of a particulate filler kneading step, a defoaming step after kneading the particulate filler, a silanated filler kneading step, and a defoaming step after kneading the silanated filler.

The particulate filler kneading step includes a step of kneading the mixed polymerizable monomer and a particulate filler at a kneading temperature of 5-60° C. for a kneading period of 5-30 minutes after charging the particulate filler into the mixed polymerizable monomer. The defoaming step after kneading the particulate filler includes a step of defoaming from the mixed polymerizable monomer and the particulate filler at 5-200 Torr for a defoaming period of 5-30 minutes.

The silanated filler kneading step includes a step of kneading the mixed polymerizable monomer, the particulate filler, and a silanated filler at a kneading temperature of 5-60° C. for a kneading period of 5-40 minutes after charging the silanated filler. The defoaming step after kneading the silanated filler includes a step of defoaming from the mixed polymerizable monomer, the particulate filler and the silanated filler at 5-200 Torr for a defoaming period of 5-30 minutes to prepare a composite material.

The composite material preserving step includes a step of preserving the 1-8 liters of composite material prepared in the composite material preparing step at preserving temperature of 1-25° C. for a preserving period of 10 days-1.5 years.

The composite material filling step includes a step of filling the composite material extruded from a nozzle using a filling machine into a small quantity preserving container having 1-50 cc of volume.

The small quantity preserving container preserving step includes a step of preserving the composite material in the small quantity preserving container at a preserving temperature of 1-40° C. for a preserving period of 50 days-5 years.

In addition to the above described steps, a defective product may be found by performing evaluation steps, thereby preventing manufacturing of a defective product. Further, these evaluation steps are important for obtaining a composite material having a stable pasty property.

The mixed polymerizable monomer evaluation step performed in the mixed polymerizable monomer preserving step is a step of performing at least one of a differential scanning calorimetry (DSC) test, a hardening test, and/or a fluidity test and preferably performing all of a differential scanning calorimetry (DSC) test, a hardening test, and a fluidity test.

The composite material evaluation step performed in the composite material preserving step is a step of performing at least one of a differential scanning calorimetry (DSC) test, a hardening test, and/or a fluidity test and preferably performing all of a differential scanning calorimetry (DSC) test, a hardening test, and a fluidity test.

The final evaluation step performed in the small amount preserving container preserving step is a step of performing at least one of a differential scanning calorimetry (DSC) test, a hardening test, and/or a fluidity test and preferably performing all of a differential scanning calorimetry (DSC) test, a hardening test, and a fluidity test.

The present disclosure provides a composite material discharged from the syringe container, which may be used under a consistent operability, includes no variation, and may keep a property stably at an early stage, at a middle stage, and at an end stage.

A pasty property of a composite material filled in a syringe container changes according to the method of use including a continuous use, an intermittent use, and the case that an unused term exists etc., and it was impossible to keep a stable pasty property.

In any case of a continuous use, an intermittent use, and the case that an unused term exists etc., the composite material discharged from the syringe container may be used under a consistent operability.

Applying a pressure to the composite material in the container means that the composite material in static condition is pressurized to become the pasty composite material having reduced thixotropy. Then, the composite material is discharged from the discharging port for releasing the pressure. According to the quantity of the force applied to the composite material, the thixotropy gradually decreases.

Once the thixotropy of the composite material decreases, even if the force such as pressure is released, the state that the thixotropy decreases is kept for a while. The thixotropy of the composite material increases by continuing the static condition. When the force such as pressure is applied to the composite material of which the thixotropy is not completely reduced, the thixotropy is completely reduced more. In the conventional composite material, it is difficult to control the thixotropy and to have a uniform pasty property of the discharged composite material. The present disclosure solves the conventional problems. The present disclosure provides a composite material which may keep for a fixed amount of time, and has a uniformly pasty property that the thixotropy decreases after discharging from the container.

Further, bubbles mixing in the composite material when filling to the small preserving container are prevented. The composite material is preserving in the preserving container in the composite material preserving step. The preserving amount of the composite material preserving container is larger than that of the small amount preserving container at the same time. This prevents the paste from a property change at the initial stage because of a decreasing surface area of the paste that contacts the outside. However, it is difficult to prevent the paste from "solidification," which is a property change at the surface. In a preferred embodiment, the composite material is filled in the small quantity preserving container before "solidification." Therefore, in a preferred embodiment, the composite material wherein the property change at the initial stage is prevented, and bubbles mixing in the composite material is prevented.

The composite material is charged into the filling machine from the preserving container in the composite material preserving step, and is continuously filled into the small amount preserving container. When the remaining amount of the composite material in the filling machine becomes low, the composite material is replenished from the preserving container of the composite material preserving step. This replenishing of the composite material from the preserving container of the composite material preserving step causes many bubbles mixing into the composite material resulting from the solidification of the surface. However, the composite material described herein reduces the bubbles mixing into the composite material during replenishing of the composite material.

Performing an inspection step in the process of preparing the composite material easily contributes a stable production of the composite material. Although performing many inspection steps contributes to a stable production of the composite material, excessive inspection steps consumes the composite material and increases the number of man hours for production. An appropriate number of inspection steps and an appropriate timing of the inspection steps were found. As a result, a defective product may be found to prevent manufacturing the defective product and to prepare the composite material efficiently.

By performing the particulate filler kneading step, a defoaming step after kneading the particulate filler, the silanated filler kneading step, and a defoaming step after kneading the silanated filler, the thixotropy of the composite material becomes stable and obtains a composite material having a uniformly pasty property.

A filler before silanation used in the embodiments is not specifically limited, and a filler known in the art such as an inorganic filler and/or an organic filler and/or an organic-inorganic composite filler, for example, may be used without restriction. The grain shape of the filler before silanation may be any shape like a sphere, a massive, a needle, a plate, a fracture, a scale, etc., and is not specifically limited. For obtaining a greater stability of the paste, the filler before silanation preferably has a sphere shape. The degree of circularity of the filler before silanation ranges from 0.7 to 1.0, preferably from 0.9 to 1.0, and more preferably from 0.95 to 1.00.

The degrees of circularity are determined by taking an image of the particles with a light microscope or a scanning electron microscope (SEM) and analyzing the image with an image analyzer. The number of fillers to be analyzed per sample may be 50 or more. The degrees of circularity are determined based on boundary lengths and area of the fillers before silanated. The degree of circularity $e=(4*\pi*S)/(L^2)$ is calculated with boundary lengths (L) and area (S) of the fillers before silanation, which are obtained by analyzing the image.

Specific examples of the inorganic filler include quartz, amorphous silica, aluminum silicate, aluminum oxide, titanium oxide, zirconium oxide, various types of glass (including glass obtained by a melting method, synthetic glass obtained by a sol-gel method, and glass generated by a gas phase reaction), calcium carbonate, talc, kaoline, clay, mica, aluminum sulfate, calcium sulfate, barium sulfate, calcium phosphate, hydroxyapatite, silicon nitride, aluminum nitride, titanium nitride, silicon carbide, boron carbide, calcium hydroxide, strontium hydroxide, and zeolite. Among these, aluminosilicate glass, borosilicate, aluminoborate, and boroaluminosilicate glass containing a heavy metal such as sodium, strontium, barium, and lanthanum and/or fluorine are preferable. The average grain size of the inorganic filler is not specifically limited, and is preferably in the range of 0.5 to 10 µM, more preferably in the range of 0.7 to 5 µM.

Ultrafine particle inorganic fillers such as aerosil generated by a gas phase method or particles of silica-zirconia oxide generated from a solution in a sol-gel reaction may also be used. Cohesive inorganic fillers obtained by agglomerating such ultrafine particles may also be used. Cohesive inorganic fillers are crushing during kneading. Crushed inorganic fillers having 1 nm to 300 nm particle diameters are classified as an ultrafine particulate inorganic filler, and crushed inorganic fillers not having 1 nm to 300 nm particle diameter are classified as an inorganic filler.

The average particle size of ultrafine particulate inorganic filler is from 1 nm to 300 nm. The ultrafine particulate inorganic filler is preferably, without any limitation, colloidal silica (trade names: Aerosil R972, Aerosil 200, Aerosil 380, Aerosil 50 (Nippon Aerosil Co., Ltd. 5-50 nm)).

The organic filler can be obtained by polymerizing a monomer having a polymerizable group, and the type of the organic filler is not specifically limited. Specific examples of the organic filler include unsaturated aromatics such as styrene, α-methylstyrene, halogenated styrene, and divinylbenzene; unsaturated esters such as vinyl acetate and vinyl propionate; unsaturated nitriles such as acrylonitrile; and substances obtained by (co)polymerizing a single or a plurality of monomers having a polymerizable group such as butadiene and isoprene. Substances obtained by polymerizing the monomers having a polymerizable group discussed earlier known in the dental field are particularly preferable. The method of manufacturing the organic filler is not specifically limited, and may be any method in which the monomers having a polymerizable group is subjected to an emulsion polymerization, a suspension polymerization, a dispersion polymerization, or the like, and may be a method in which a polymer bulk generated in advance is pulverized. Organic-inorganic composite fillers in which inorganic particles are contained in an organic polymer may also be used. The inorganic particles to be contained in the organic polymer are not specifically limited, and those known in the art may be used. Examples of the inorganic particles include particles of the inorganic fillers discussed above. The method of manufacturing the organic-inorganic composite filler is also not specifically limited, and any method may be used. Examples of the method include a method in which the surfaces of the inorganic particles are microencapsulated or grafted with the organic substance, a method in which the inorganic particles are subjected to a radical polymerization after a polymerizable functional group or a polymerization initiating group is introduced into the surfaces of the inorganic particles, and a method in which a polymer bulk containing inorganic particles generated in advance is pulverized.

The average grain size of the organic filler or the organic-inorganic composite filler is preferably in the range of 1 to 100 μm, more preferably 3 to 50 μm, further more preferably 5 to 30 μm. The inorganic, organic, and organic-inorganic composite fillers may be used singly or in combination of several kinds thereof.

After the surfaces of the particles of the filler, such as the inorganic, organic, or organic-inorganic composite filler, are treated by a method known in the art, the filler can be used for a composite material. The surface treatment may be performed using a surfactant, fatty acid, organic acid, inorganic acid, a silane coupling agent, a titanate coupling agent, polysiloxane, or the like, for example. A preferable surface treatment method improves the wettability between the resin component and the surface of the filler and imparts superior properties to the composite material, and can be selected as appropriate according to the required properties. The surface of the filler may be subjected, without restriction, to a surface treatment performed using a special surface treatment agent and/or by a special surface treatment method for the purpose of increasing the functionality of the filler.

A silanated filler provided by a silanation step in which a filler is treated with a silane coupling agent is preferably used. Further, the silanated filler is preferably provided through a silanated filler preserving step in which a silanated filler is preserved for a predetermined period.

The silanation step includes a step of preparing a silane treatment liquid containing 1-40% of silane coupling agent, and 60-99% of organic solvent and/or water, and a step of treating a filler with the silane treatment liquid. The filler and the silane treatment liquid are charged into a treatment container and the filler is silanated at a treatment temperature of 1-60° C. for a treatment period of 1 minute-24 hours. The silane treatment liquid is charged in a ratio of 1-15 volume % based on the volume of the filler. As a result of silanation, the silanated filler may be a slurry. The silane treatment liquid is preferably charged by spraying or dripping.

An aggregate is provided by drying the treated material at a drying temperature of 60-200° C. for a drying period of 1-120 hours. The silanated filler is provided by crushing the aggregate.

The silane treatment liquid preferably contains 5-30% of silane coupling agent, 50-70% of organic solvent and/or 0.5-25% of water.

As the silane coupling agent, there can be preferably used, not particularly limited to, methyltrimethoxysilane, methyltriethoxysilane, methyltrichlorosilane, dimethyldichlorosilane, trimethylchlorosilane, hexamethyldisilazane, vinyltrimethoxysilane, vinyltriethoxysilane, vinyltrichlorosilane, vinyltriacetoxysilane, vinyltris((3-methoxyethoxy)silane, γ-methacryloyloxypropyltrimethoxysilane, γ-methacrloyloxypropyltris(β-methoxyethoxy)silane, γ-chloropropyltrimethoxysilane, γ-chloropropylmethyldimethoxysilane, γ-glycidoxypropyltrimethoxysilane, γ-glycidoxypropylmethyldiethoxysilane, β-(3,9-epoxycyclohexyl)ethyltrimethoxysilane, N-phenyl-γ-aminopropyltrimethoxysilane and hexamethyldisilazane. Particularly preferably are methyltrichlorosilane, dimethyldichlorosilane and hexamethyldisilazane.

An organic solvent is preferably a volatile water-soluble organic solvent. As the volatile water-soluble organic solvent, there can be exemplified methanol, ethanol, n-propanol, isopropyl alcohol, acetone, methyl ethyl ketone and the like. As required, these organic solvents can be used in a plural kinds being mixed together. By taking toxicity to a living body into consideration, it is desired to use ethanol, isopropyl alcohol and acetone.

The silanated filler preserving step includes a step of preserving a silanated filler for a preserving period of 30-600 days. When a preserving period is short, matching with resin deteriorates. Therefore, it is difficult to prepare a smooth paste, and it is difficult to prepare a stable paste.

When a preserving period lasts for a long term, the effect of the silane coupling agent fades and it is difficult to prepare a stable paste.

The silanated filler is preserved in a hermetic container. The volume of the container is 10-50 liters. The container is preferably made of polyethylene and formed into bag-shape.

The preserving temperature is at 1-50° C. and is preferably at 5-25° C. Preserving at high temperatures obstructs the effect of the silane coupling agent.

A proportion of the silanated filler in a composite material may be optionally selected depending upon a material property required for a composite material. An filling amount of low-viscous materials such as sealants, bonding materials, primers, tooth surface treating agents, opacifying agents and cements generally used in the dental field should be set at a relatively small level since higher fluidity required as material property is required for these materials. Therefore, the amount is preferably in a range of 5.0-80.0 parts by weight, more preferably in a range of 30.0-70.0 parts by weight relative to the whole component of the composite material. In addition, a filling amount of high-viscous materials such as a composite resin and a veneer crown resin should be set at a relatively high level since, as the required material property, such the shapability is required that does not cause deformation after shape adjustment. Accordingly, the amount is preferably in a range of 50.0-98.0 parts by weight, more preferably in a range of 75.0-98.0 parts by weight relative to the whole component of a composite material.

The polymerizable monomer used in the embodiments may be, without any limitation, known monofunctional or multifunctional polymerizable monomers that are generally used for composite material. The polymerizable monomers are preferably those having an acryloyl group and/or a methacryloyl group.

Examples of polymerizable monomers having no acidic group include:

monofunctional monomers (non-crosslinkable monomers), e.g., (meth)acrylic acid esters such as methyl(meth)acrylate, ethyl(meth)acrylate, butyl(meth)acrylate, hexyl(meth)acrylate, tetrahydrofurfuryl(meth)acrylate, 2-hydroxyethyl(meth)acrylate, glycidyl(meth)acrylate, lauryl(meth)acrylate, cyclohexyl(meth)acrylate, benzil(meth)acrylate, allyl(meth)acrylate, 2-ethoxyethyl(meth)acrylate, methoxy polyethylene glycol(meth)acrylate, glycerol(meth)acrylate and isobornyl(meth)acrylate; silane compounds such as .gamma.-(meth)acryloyloxypropyltrimethoxysilane and .gamma.-(meth)acryloyloxypropyltriethoxysilane; nitrogen-containing compounds such as 2-(N,N-dimethylamino)ethyl(meth)acrylate, N-methylol(meth)acrylamide and diacetone(meth)acrylamide, aromatic bifunctional monomers (crosslinkable monomers), e.g., 2,2-bis(4-(meth)acryloyloxyphenyl)propane, 2,2-bis(4-(3-(meth)acryloyloxy-2-hydroxypropoxy)phenyl)propane, 2,2-bis(4-(meth)acryloyloxyethoxyphenyl)propane, 2,2-bis(4-(meth)acryloyloxydiethoxyphenyl)propane, 2,2-bis(4-(meth)acryloyloxytetraethoxyphenyl)propane, 2,2-bis(4-(meth)acryloyloxypentaethoxyphenyl)propane, 2,2-bis(4-(meth)acryloyloxydipropooxyphenyl)propane, 2(4-(meth)acryloyloxyethoxyphenyl)-2-(4-(meth)acryloyloxydiethoxyphenyl) propane, 2-(4-(meth)acryloyloxydiethoxyphenyl)-2-(4-(meth)acryloyloxytriethoxyphenyl)propane, 2-(4-(meth)acryloyloxydipropoxyphenyl)-2-(4-(meth)acryloyloxytriethoxyphenyl)propane, 2,2-bis(4-(meth)acryloyloxydipropoxyphenyl)propane and 2,2-bis(4-(meth)acryloyloxyisopropoxyphenyl)propane, aliphatic bifunctional monomer (crosslinkable monomers), e.g., 2-hydroxy-3-acryloyloxypropylmethacrylate, hydroxypivalic acid neopentylglycol di(meth)acrylate, ethylene glycol di(meth)acrylate, diethylene glycol di(meth)acrylate, triethylene glycol di(meth)acrylate, butylene glycol di(meth)acrylate, polyethylene glycol di(meth)acrylate, neopentyl glycol di(meth)acrylate, propylene glycol di(meth)acrylate, 1,3-butanediol di(meth)acrylate, 1,4-butanediol (meth)acrylate, 1,6-hexanediol di(meth)acrylate, and glycerin di(meth)acrylate, trifunctional monomer (crosslinkable monomers), e.g., trimethylolpropane tri(meth)acrylate, treimethylolethane tri(meth)acrylate, trimethylolmethane tri(meth)acrylate and pentaerythritol tri(meth)acrylate, tetrafunctional monomer (crosslinkable monomers), e.g., pentaerythritol tetra(meth)acrylate and ditrimethylolporpane tetra(meth)acrylate.

Examples of urethane-based polymerizable monomers may include di(meth)acrylates having a bifunctional or trifunctional or more-functional urethane linkage that are derived from an adduct of a polymerizable monomer having a hydroxy group such as 2-hydroxyethyl(meth)acrylate, 2-hydroxypropyl(meth)acrylate and 3-chloro-2-hydroxypropyl(meth)acrylate, and a diisocyanate compound such methylcyclohexane diisocyanate, methylene bis(4-cyclohexyl isocyanate), isophorone diisocyanate, diisocyanate methylbenzene and 4,4-diphenylmethane diisocyanate.

In addition to the aforementioned (meth)acrylate-based polymerizable monomers, other polymerizable monomers, for example, a monomer, an oligomer or a polymer having at least one polymerizable group in the molecule may be used for polymerizable monomers of the composite material if desired. The polymerizable monomers other than the (meth)acrylate-based polymerizable monomers may have a substituent such as an acidic group and a fluoro group in the molecule. In the embodiments, the polymerizable monomer is not necessarily of a single component, and may be a mixture of a plurality of polymerizable monomers. If the viscosity of the polymerizable monomer at room temperature is extremely high, or if the polymerizable monomer is solid, the polymerizable monomer is preferably combined with a polymerizable monomer with low viscosity to be used as a mixture of the polymerizable monomers. The combination is not limited to a combination of two kinds, and may be a mixture of three or more kinds.

The polymerizable monomers of the composite material may include only monofunctional polymerizable monomers, and may additionally include polyfunctional polymerizable monomers. A preferred polymerizable monomers may include an aromatic bifunctional polymerizable monomer and an aliphatic bifunctional polymerizable monomer. More preferably, the polymerizable monomers may includes 2,2-bis(4-(3-methacryloyloxy-2-hydroxypropoxy)phenyl)propane (Bis-GMA) and triethylene glycol dimethacrylate (TEGDMA).

In the embodiments, the polymerizable monomers may include polymerizable monomers containing an acid group such as phosphoric acid group, carboxylic acid group, phosphonic acid, sulfonic acid group or the like in the molecule as a part or the whole of the polymerizable monomers so that the composite material can adhere to the teeth substance and a nonprecious metal. In order to enhance the property to adhere a precious metal, the polymerizable monomers may include a polymerizable monomer containing a sulfur atom in the molecule.

The polymerizable monomers discussed above may include carboxylilc acid group-containing polymerizable monomers, e.g., (meth)acrylic acid, 1,4-di(meth)acryloyloxyethyl-pyromellitic acid, 6-(meth)acryloyloxynaphtalene-1,2,6-tricarboxylic acid, N-(meth)acryroyl-p-aminobenzoic acid, N-(meth)acryroyl-5-aminosalicylic acid, 4-(meth)acryroyloxyethyltrimellic acid and anhydride thereof, 4-(meth)acryroyloxybutyltrimellic acid and anhydride thereof, 2-(meth)acryroyloxybenzoic acid, β-(meth)acryroyloxyethyl hydrogen succinate, β-(meth)acryroyloxyethyl hydrogen maleate, 11-(meth)acryloyloxy-1,1-undecanedicarboxylic acid and p-vinylbenzoic acid; phosphate group-containing monomers, e.g., 2-(meth)acryloyloxyethyl hydrogen phosphate, 3-(meth)acryloyloxypropyl dihydrogen phosphate, 10-(meth)acryloyloxydecyl hydrogen phosphate, bis(2-(meth)acryloyloxyethyl)dihydrogen phosphate and 2-(meth)acryloyloxyphenyl hydrogen phosphate; sulfonic group-containing monomers, e.g., 2-(meth)acrylamide-2-methylpropanesulfonic acid, 4-(meth)acryloyloxybenzenesulfonic acid and 3-(meth)acryloyloxypropanesulfonic acid; sulfur atom-containing monomers, e.g., (meth)acrylate having a triazinethiol group, (meth)acrylate having a mercapto group, (meth)acrylate having a polysulfide group, (meth)acrylate having a thiophosphate group, (meth)acrylate having a disulfide cyclic group, (meth)acrylate having a mercaptodithiazole group, (meth)acrylate having a thiouracil group and (meth)acrylate having a thiirane group. These polymerizable monomers may be used alone or in mixture of two or more kinds.

A known radical generator may be used as a polymerization initiator in the embodiments. Polymerization initiators are generally classified into chemical polymerization initiators that initiates polymerization by mixing the same with the monomers upon use, thermal polymerization initiators that initiates polymerization by heating or warming the composition, and photoinitiators that initiates polymerization by light irradiation.

Among such polymerization initiators, examples of chemical polymerization initiators may include redox type polymerization initiator systems comprising an organic peroxide/an amine compound or an organic peroxide/an amine compound/a sulfinic acid salt, or an organic peroxide/an amine compound/a borate compound, and organometal type initiator systems that initiate polymerization by reacting with oxygen or water.

Examples of the aforementioned organic peroxides may include benzoylperoxide, parachlorobenzoylperoxide, 2,4-dichlorobenzoyl peroxide, acetyl peroxide, lauroyl peroxide, tertiary-butyl peroxide, cumene hydroperoxide, 2,5-dihydroperoxy-2,5-dimethylhexane, methyl ethyl ketone peroxide, and tertiary-butyl peroxide benzoate.

Examples of the aforementioned amine compounds may include a secondary or tertiary amine in which an amine group is bound to an aryl group, and particular examples thereof are p-N,N-dimethyltoluidine, N,N-dimethylaniline, N-β-hydroxyethylaniline, N,N-di(β-hydroxyethyl)aniline, p-N,N-di(β-hydroxyethyl)toruidine, N-methylaniline, and p-N-methyltoluidine.

Examples of the aforementioned sulfuric acid salts may include sodium benzenesulfinate, lithium benzenesulfinate, and sodium p-toluenesulfinate.

Examples of the aforementioned borate compounds include, trialkylphenylboron, and a sodium salt, a lithium salt, a potassium salt, a magnesium salt, a tetrabutyl ammonium salt and a tetramethyl ammonium salt of trialkyl(p-fluorophenyl)boron (wherein the alkyl group is n-butyl group, n-octyl group, n-dodecyl group or the like).

Examples of the aforementioned organometal type polymerizable initiators may include organic boron compounds such as triphenylborane, tributylborane, and a partial oxide of tributylborane.

Azo compounds such as azobisisobutyronitrile, methyl azobisisobutyrate and azobiscyano valeric acid may be used as a thermal polymerization initiator used in the embodiments in addition to the aforementioned organic peroxide.

The photoinitiator used in the embodiments may be a photosensitizer. The photosensitizer may be used alone or in combination with a photopolymerization promotor. Examples of the aforementioned photosensitizers may include α-diketones such as benzil, camphorquinone, α-naphtil, acetonaphtone, p,p'-dimethoxybenzil, p,p'-dichlorobenzylacetyl, pentadione, 1,2-phenanthrenquinone, 1,4-phenanthrenquinone, 3,4-phenanthrenquinone, 9,10-phenanthrenquinone and naphthoquinone; benzoin alkyl ethers such as benzoin, benzoin methyl ether and benzoin ethyl ether; thioxanthones such as thioxanthone, 2-chlorothioxanthone, 2-methylthioxanthone, 2-isopropylthioxanthone, 2-methoxythioxanthone, 2-hydroxythioxanthone, 2,4-diethylthioxanthone and 2,4-diisopropylthioxanthone; benzophenones such as benzophenone, p-chlorobenzophenone and p-methoxybenzophenone; acylphosphineoxides such as 2,4,6-trimethylbenzoyl diphenylphosphineoxide and bis(2,6-dimethoxybenzoyl)-2,4,4-trimethylpentylphosphineoxide; α-aminoacetophenones such as 2-benzyl-dimethyl-amino-1-(4-morpholinophenyl)-butanone-1,2-benzyl-diethyl-amino-1-(4-morpholinophenyl)propanone-1; ketals such as benzyldimethylketal, benzyldiethylketal and benzyl (2-methoxyethylketal); titanocenes such as bis(cyclopentadienyl)-bis[2,6-difluoro-3-(1-pyrolyl)phenyl]titanium, bis(cyclopentadienyl)-bis(pentanefluorophenyl)titanium and bis(cyclopentadienyl)-bis(2,3,5,6-tetrafluoro-4-disiloxyphenyl)-titanium.

Examples of the aforementioned photopolymerization promotors may include tertiary amines such as N,N-dimethylaniline, N,N-diethylaniline, N,N-di-n-butylaniline, N,N-dibenzylaniline, p-N,N-dimethyl-toluidine, m-N,N-dimethyltoluidine, p-N,N-diethyltoluidine, p-bromo-N,N-dimethylaniline, m-chloro-N,N-dimethylaniline, p-dimethylaminobenzaldehyde, p-dimethylaminoacetophenone, p-dimethylaminobenzoic acid, p-dimethylaminobenzoicacid ethyl ester, p-demtethylaminobenzoic acid amino ester, N,N-dimethylanthranilic acid methyl ester, N,N-dihydroxyethylaniline, p-N,N-dihydroxyethyl-toluidine, p-dimethylaminophenylalcohol, p-dimethylaminostyrene, N,N-dimethyl-3,5-xylidine, 4-dimethylaminopyridine, N,N-dimethyl-α-naphthylamie N,N-dimethyl-β-naphthylamine, tributylamine, tripropylamine, triethylamine, N-methyldiethanolamine, N-ethyldiethanolamine, N,N-dimethylhexylamine, N,N-dimethyldodecylamine, N,N-dimethylstearylamine, N,N-dimethylaminoethyl methacrylate, N,N-diethylaminoethyl methacrylate and 2,2'-(n-butylimino) diethanol; secondary amines such as N-phenylglycine; barbituric acids such as 5-butylbarbituric acid and 1-benzyl-5-phenylbarbituric acid; tin compounds such as dibutyltin diacetate, dibutyltin dilaurate, dioctyltin dilaurate, dioctyltin diperacetate, dioctyltin bis(mercaptoacetic acid isooctyl ester) salt and tetramethyl-1,3-diacetoxydistannoxane; aldehyde compounds such as laurylaldehyde and terephthalaldehyde; sulfur-containing compounds such as dodecylmercaptan, 2-mercaptobenzooxazole, 1-decanethiol and thiosalicylic acid.

The composite material of the present invention may further include an oxycarboxylic acid such as citric acid, maleic acid, tartaric acid, glycolic acid, gluconic acid, α-oxyisobutyric acid, 2-hydroxypropioic acid, 3-hydroxybutanoic acid, 4-hydroxybutanoic acid, and dimethylolpropioic acid to improve the photopolymerization promoting ability.

Those polymerization initiators used in the embodiments may be used alone or as a mixture of two or more thereof. In addition, these polymerization initiators may be used in combination irrespective of the polymerization form and the kind of polymerization initiators. The amount of a polymerization initiator to be added may be appropriately determined depending upon the use. In general, the amount may be selected from a range of 0.1-10 parts by weight based on a polymerizable monomer.

The polymerization initiator is preferably a photopolymerization initiator. The composite material that comprises a photopolymerization initiator is relatively easy to be polymerized without substantial air bubble entrainment. The photopolymerization initiator is preferably a combination of an α-diketone and a tertiary amine and more preferably, a combination of camphorquinone with an aromatic amine having an amino group directly bound to the benzene ring such as ethyl p-N,N-dimethylaminobenzoate or with an aliphatic amine having a double bond in the molecule such as N,N-dimethylaminoethyl methacrylate. The composite material, in embodiments, may comprise, depending upon the use, a sensitizing pigment such as coumalin, cyanine, and thiazine; a light acid generator which produces Broensted acid or Lewis acid by light irradiator such as a s-triazine derivative substituted with a halomethyl group or diphenyl iodonium salt compound; quaternary ammonium halides; and transition metal compound.

The composite material according to embodiments is prepared by mixing a silanated filler, a polymerizable monomer, and a polymerization initiator.

The composite materials may be colored with a coloring pigment in accordance with a product property. The coloring pigments are classified into inorganic pigments and organic pigments. Examples of inorganic pigments may include chromates such as chrome yellow, zinc yellow and barium yellow; ferrocyanides such as Prussian blue; sulfides such as vermilion, cadmium yellow, zinc sulfide, antimony white and cadmium red; sulfates such as barium sulfate, zinc sulfate and strontium sulfate; oxides such as zinc white, titanium white, blood red, black iron oxide and chromium oxide; hydroxides such as aluminum hydroxide; silicates such as calcium silicate and ultramarine; and carbons such as carbon block and graphite. Examples of organic pigments may include nitoroso pigments such as Naphthol Green B and Naphthol Green Y; nitoro pigments such as Naphthol S and Lithol Fast Yellow 2G; insoluble azo pigments such as Permanent Red 4R, Brilliant Fast Scarlet, Hanza Yellow and Benzidine Yellow; poorly-soluble azo pigments such as Lithol Red, Lake Red C and Lake Red D; soluble azo pigments such as Brilliant Caramine 6B, Permanent Red F5R, Pigment. Scarlet 3B and Bordeaux 10B; phthalocyanine pigments such as Phthalocyanine Blue, Phthalocyanine Green and Sky Blue; basic dye pigments such as Rhodamine Lake, Malachite Green Lake and Methyl Violet Lake; and acidic dye pigments such as Peacock Blue Lake, Eosin Lake and Quinoline Yellow Lake. These pigments may be used alone or in combination of two or more thereof. In an embodiment, the coloring pigment is preferably an inorganic pigment, preferably titanium white, blood red, black iron oxide or yellow iron oxide.

The composite material described herein may comprise an ultraviolet absorbing agent such as 2-hydroxy-4-methylbenzophenone; polymerization inhibitors such as a hydroquinone, a hydroquinone monomethyl ether, 2,5-di(tertiary-butyl)-4-methylphenol, and butyrated hydroxyltoluene (BHT); an anti-discoloring agent; an antimicrobial agent; and the other conventional known additives. The composite material may be packed in a single package, or divided into two packs or the other type packages. The package of the composite material may be determined depending upon the kind of polymerization initiator or the use.

The effect of the composite material is provided by a process that comprises at least in order of a mixed polymerizable monomer preparing step, a mixed polymerizable monomer preserving step, a composite material preparing step, a composite material preserving step, a composite material filling step, and a small quantity preserving container preserving step.

Hereinafter, each process will be sequentially described.

A mixed polymerizable monomer preparing step includes at least a step of mixing a polymerizable monomer and a polymerization initiator to prepare a mixed polymerizable monomer, but the method of mixing is not particularly limited. It is necessary that a mixed polymerizable monomer prepared in the mixed polymerizable monomer preparing step is in a uniform state after mixing. Therefore, it is necessary to mix so that there are no remainders such as a polymerization initiator. Preferably, a mixed polymerizable monomer preparing step does not include a defoaming step. A defoaming step is a step of defoaming air bubbles by reducing the pressure below the atmospheric pressure after mixing, which is often performed at atmospheric pressure. Performing a defoaming step may deteriorate a polymerizable monomer, causes a reduction of the characteristic of a physical property, and some polymerizable monomers may harden.

Further, it is necessary to charge a polymerization initiator into a mixed polymerizable monomer. To charge a polymerization initiator into a mixed polymerizable monomer causes a reduction of the characteristic of a physical property and some polymerizable monomers may be harden. Therefore, an excessive amount of a polymerization initiator cannot be mixed.

A mixing volume of the mixed polymerizable monomer is 1-50 liters per batch and is preferably 5-11 liters per batch. When the mixing volume is small, not only a production process becomes longer but also a stable production of a mixed polymerizable monomer becomes difficult. When a mixing volume is large, a polymerizable monomer often deteriorates and the stability of the properties is affected.

A blender used in the method described in the embodiments is not specifically limited, and is preferably a mixer that mixes a polymerizable monomer and a polymerization initiator in a mixing container with a blade. More preferably, a blender is a tumbler mixer that mixes a polymerizable monomer and a polymerization initiator by rotation or swing a mixing container. A deterioration of the contents in the blender may be reduced by using a tumbler mixer. Although the mixing period is varied according to the blender, the mixing period is preferably for 1 minute-24 hours, is more preferably for 15 minutes-10 hours. The mixing temperature is at 1-60° C., preferably at 5-30° C.

When a polymerization initiator used in the composite material is a chemical polymerization initiator, low temperature mixing is preferred and the mixing temperature is at 5-10° C.

During the mixing in this step, an additive agent such as a polymerization inhibitor, an antitarnish agent, an antimicrobe agent, and an ultraviolet absorber is preferably mixed at the same time. This prevents the deterioration of the composite material and contributes to the stability of the composite material.

A permeability of a mixed polymerizable monomer is preferably 80-100%. When a composite material is used as a dental material, a stable color reproducibility is required even though a composite material is colored with coloring materials, and the variations in color between lots become a problem. Stable color tone stability is obtained as a permeability of the mixed polymerizable monomer is high.

A mixed polymerizable monomer preserving step includes a step of preserving a mixed polymerizable monomer prepared in the mixed polymerizable monomer preparing step. A mixed polymerizable monomer is preserved in a mixed polymerizable monomer preserving container. The volume of preserved mixed polymerizable monomer is 1-50 liters, preferably 5-11 liters.

When a tumbler mixer is used in the mixed polymerizable monomer preparing step, the tumbler mixer is preferably used as a mixed polymerizable monomer preserving container as it is.

A mixed polymerizable monomer preserving container is preferably made of a resin and is preferably made of polyethylene. Further, a mixed polymerizable monomer preserving container is preferably translucent and is preferably excellent in a shading property. More preferably, a mixed polymerizable monomer preserving container has shading rate of no less than 99.99%. The shading rate of no less than 99.99% may be reproduced by using an aluminum foil for enhancing a shading property. A mixed polymerizable monomer preserving container is preferably a hermetic container.

A preserving temperature of the mixed polymerizable monomer preserving container is at 1-35° C., and is preferably at 1-10° C. in a dark and cool place. A preserving period of a mixed polymerizable monomer preserving container is for 10 days-1.5 years, preferably for 30 days-1 year.

A mixed polymerizable monomer may be stabilized by preserving to obtain a uniformly mixed polymerizable monomer. Further, a kneading period may be shortened and a stable paste may be prepared. When a preserving period is over 1.5 years, deterioration of a mixed polymerizable monomer occurs and a mixed polymerizable monomer becomes a non-uniform state. When a preserving period is within one year, deterioration of a mixed polymerizable monomer is not observed and a uniform mixed polymerizable monomer may be obtained and a stable composite material may be prepared.

The mixed polymerizable monomer preserving step preferably includes a mixed polymerizable monomer evaluation step. A defective semi product is detected by inspecting a semi product in a manufacturing process to increase a manufacturing yield of a final product.

A mixed polymerizable monomer evaluation step performed in a mixed polymerizable monomer preserving step is a step of evaluating the mixed polymerizable monomer formed in the mixed polymerizable monomer preserving step. After the mixing in the mixed polymerizable monomer preparing step, the mixed polymerizable monomer is divided, and a portion of the mixed polymerizable monomer is placed in a mixed polymerizable monomer evaluation container that is different from a mixed polymerizable monomer preserving container. A mixed polymerizable monomer may be divided directly from the mixed polymerizable monomer preserving container. A mixed polymerizable monomer is preferably divided into the mixed polymerizable monomer evaluation container immediately after a mixed polymerizable monomer preparing step. When a mixed polymerizable monomer is divided from the mixed polymerizable monomer evaluation container right away, a evaluation of a mixed polymerizable monomer may be more likely to be performed without problems.

In the mixed polymerizable monomer evaluation step, a differential scanning calorimetry (DSC) test, a hardening test, and/or a fluidity test or the like is preferably performed. Each test is performed by a measurement method known in the art to determine the acceptance or rejection. Acceptance or rejection is determined based on whether the test result is within a predetermined range. A detailed test method of the hardening test, and the fluidity (flow) test will be described in "characteristic confirmation test method" below.

Although the predetermined range is important for determining the stability of the mixed polymerizable monomer, the predetermined range is widely changed depending on the species of the mixed polymerizable monomer etc.

By evaluating the divided mixed polymerizable monomer in the mixed polymerizable monomer evaluation container, the mixed polymerizable monomer preserved in the mixed polymerizable monomer preserving container may be evaluated.

The composite material preparing step includes a step of kneading the mixed polymerizable monomer and the silanated filler to prepare the composite material. The mixing method is not particularly limited. It is necessary that the composite material prepared in the composite material preparing step is in a uniform state after mixing.

An ordinary kneading machine may be used as a kneader. Preferably, a kneader (Inoue Seisakusho Co., Ltd etc) is used for preparing a high viscosity composite material, and a planetary mixer (Inoue Seisakusho Co., Ltd etc) is used for preparing a low viscosity composite material.

Although a kneading container accompanies a kneading machine, the volume of a kneading container is 0.5-50 liters, preferably 2-20 liters.

A charging amount for a kneading machine is 30-70% of the volume of the kneading machine, preferably 40-60% of the volume of the kneading machine. When there are many charging amounts or small charging amounts, a kneading is not properly performed to generate a uniform composite material.

Depending on intended pasty property, a ratio for charging the mixed polymerizable monomer and the silanated filler are 0.1-9 parts by weight of the silanated filler and 0.01-0.2 parts by weight of a particulate filler, based on 1 part by weight the mixed polymerizable monomer.

More specifically, the mixed polymerizable monomer is 1-3 liters, the silanated filler is 1-6 kg, and the particulate filler is 30-500 g. The composite material preparing step includes a kneading step, and a defoaming step, and a more detailed embodiment is described below.

The composite material preparing step includes a step of charging the silanated filler after charging the mixed polymerizable monomer into the kneading container, and then a step of performing the kneading step and the defoaming step. The kneading step is a step of performing a kneading work, and the defoaming step is a step of performing a defoaming work.

It is important that the mixed polymerizable monomer is charged before charging the silanated filler, thereby shortening the kneading period to prevent the generation of variation.

The composite material is preferably prepared using the particulate filler. In this case, the composite material preparing step includes a step of charging the particulate filler after charging the mixed polymerizable monomer, a step of performing a particulate filler kneading step, a defoaming step after kneading the particulate filler, a step of charging the silanated filler, and a step of performing a silanated filler kneading step and a defoaming step after kneading the silanated filler. Kneading may be facilitated by separating the charging the particulate filler and the silanated filler into multiple times. When the charging of the silanated filler is divided into multiple times, although the defoaming may be performed after kneading every time, the defoaming is preferably performed after charging all silanated fillers.

Kneadability of the particulate filler with the mixed polymerizable monomer is poor. Therefore, the particulate filler and the mixed polymerizable monomer sometimes are not kneaded enough. In some cases, a particulate filler kneading confirmation step is preferably performed, which confirms that the kneaded product prepared by the particulate filler kneading step and the defoaming step after particulate filler kneading has transparency, and the kneaded product was sufficiently kneaded and defoamed. If the composite material is prepared without the particulate filler kneading confirmation step, there may be a part where the particulate filler was not sufficiently mixed. It may cause a variation in the final product of the composite material. Further, it is difficult to obtain a stable paste if there is a variation caused by insufficient mixing. It is not preferable that the silanated filler is charged before the kneading of an ultrafine particle filler, because it is difficult to perform a particulate filler kneading confirmation step. The silanated filler is preferably charged after the kneading the ultrafine particle filler.

It is necessary to knead the mixed polymerizable monomer and the ultrafine particle filler until the whole is in the uniform state. If the paste has transparency after a defoaming step after kneading the particulate filler, the paste may be considered to be uniform. When it is not uniform, the kneading and the defoaming are repeated. If non-transparent ultrafine particle filler remains in the kneaded paste, it is necessary to remove a part where the non-transparent ultrafine particle filler remains, or to stop producing the kneaded product. Similar work can be performed if the paste is semitransparent, even if the paste is not completely transparent.

In the silanated filler kneading step, the silanated filler is kneaded with the mixed polymerizable monomer or the kneaded product of the mixed polymerizable monomer and the ultrafine particle filler until becoming a uniform paste. In the defoaming step, air bubbles in the composite material are removed. Therefore, defoaming is preferably performed while mixing them.

It is necessary to perform a defoaming step after kneading the silanated filler for defoaming air bubbles in the composite material. The defoaming step is preferably a step of defoaming air bubbles by reducing the vacuum to 5-200 Torr in the kneading container. In this defoaming step, air bubbles in the composite material expand thereby causing foaming of the composite material. The defoaming step is generally performed while kneading in order to break the air bubbles. A kneading speed for breaking air bubbles is preferably adjusted in accordance with the braking condition of air bubbles. A kneading condition is preferably determined by adjusting kneading speed with depression speed. The kneading is preferably performed while adjusting a degree of depressurization The kneading period and the kneading temperature may be optionally set. For example, it is preferable to perform the particulate filler kneading step at a kneading temperature 5-60° C. for a kneading period 5-30 minutes after charging the particulate filler, the defoaming step after kneading the particulate filler at a vacuum degree of 5-200 Torr of for a kneading period 5-30 minutes, the silanated filler kneading step at a kneading temperature of 5-60° C. for kneading period of 5-40 minutes after charging the silanated filler, and the defoaming step after kneading the silanated filler at a vacuum degree of 5-200 Torr for a kneading period 5-30 minutes.

When the polymerization initiator is a chemical polymerization initiator, low temperature mixing is preferred. In this case, the kneading step is preferably performed at a kneading temperature of 1-25° C., 1° C.-room temperature, or 5-23° C. for a kneading period of 5-30 minutes, in this case. Further, in the defoaming step, the kneading is performed at a kneading temperature of 1-25° C., 1° C.-room temperature, or 5-23° C. for a kneading period of 5-30 minutes at a vacuum degree of 60-200 Torr.

These kneading periods and kneading temperature differ depending on the species of the kneader or the planetary mixer.

The composite material preserving step includes a step of preserving the composite material prepared in the composite material preparing step.

The composite material is preserved in the composite material preserving container. The volume of composite material preserved in in the composite material preserving container is 1-50 cc, and preferably 2-5 cc. with is 1-8 liters, is preferably 2-5 liters.

The composite material is divided into the composite material preserving container from the mixing container that is used in the composite material preparing step.

The composite material preserving container is preferably made of a resin and is preferably made of polyethylene. Further, the composite material preserving container is preferably translucent and is preferably excellent in shading property. More preferably, the composite material preserving container has shading rate of no less than 99.99%. The shading rate of no less than 99.99% may be reproduced by using an aluminum foil for enhancing a shading property. The composite material preserving container is preferably a hermetic container.

The preserving temperature of the composite material preserving container that preserves the composite material prepared by the composite material preparing step, is at 1-25° C., and is preferably at 1-8° C. in a dark and cool place. The preserving period of the composite material preserving container that preserves the composite material prepared by the composite material preparing step is 10 days-1.5 years, is preferably 30 days-1 year.

The composite material is stabilized by preserving to obtain the composite material having a uniformly pasty property. When a preserving period of the composite material preserving container is over 1.5 years from a point of time when the composite material is filled in the composite material preserving container, a preserving period of the small quantity preserving container used by dentists and dental technicians, which are the final user, becomes shorter because the deterioration of the composite material occurs and the pasty property of the composite material is in a non-uniform state. When the preserving period is within one year from a point of time when the composite material is filled in the composite material preserving container, the deterioration of the composite material is not observed and the composite material that is a uniform may obtain and a paste having a stable pasty property may be prepared.

The composite material preserving step preferably includes a composite material evaluation step. A defective semi product is detected by inspecting a semi product in a manufacturing process to increase a manufacturing yield of a final product.

The composite material evaluation in the composite material evaluation step may be performed as follows. After kneading of the composite material preparing step, a portion of the composite material is divided into the composite material evaluation container that is different from the composite material preserving container. The composite material is preferably divided into the composite material evaluation container immediately after the kneading of the composite material preparing step. When the composite material is directly divided from the kneading container, the evaluation of the composite material may be more likely to be performed without problems.

In the composite material evaluation step, a differential scanning calorimetry (DSC) test, a hardening test, and/or a fluidity test or the like is preferably performed. Each test is performed by a measurement method that is known in the art to determine the acceptance or rejection. Acceptance or rejection is determined based on whether the test result is within a predetermined range. Although the predetermined range is important for determining the stability of the composite material, the predetermined range may be widely changed depending on the species of the composite material etc. A detail test method of a hardening test, and a fluidity (flow) test will be described in "characteristic confirmation test method" below.

By evaluating the divided composite material from the composite material evaluation container, the composite material in the composite material preserving container may be evaluated. The composite material filling step includes a step of filling the composite material preserved in the composite material preserving container into a small quantity preserving container.

The small quantity preserving container is a container that may be used on the end user side, and is generally called a syringe container. The volume of the syringe container is in a range of 1-200 cc. When using the composite material having a low viscosity, a syringe container may be a cylindrical injector type and the composite material maybe discharged from the tip nozzle of the cylindrical injector type by pushing a stick. When using the composite material having a high viscosity, a syringe container may be a cylindrical injector type as is the case in a low viscosity, but the composite material may be discharged by screwing a stick. A small quantity syringe container may be a compule, which is a single use container for cavity-filling. All of these containers are a cylindrical container that discharge the composite material pushed by a piston. When a composite material discharging port of the cylindrical container is sharpened, the effect of composite material is remarkable.

The composite material is preserved in a small quantity preserving container. The volume of mixed polymerizable monomer in the small quantity preserving container is 1-50 cc, and preferably 2-5 cc.

The small quantity preserving container is preferably made of resin, is more preferably made of polyethylene.

Further, the small quantity preserving container is preferably translucent and is preferably excellent in shading property. More preferably, the small quantity preserving container has shading rate of no less than 99.99%, and is a hermetic container.

The composite material may be pushed out by pushing the stick of the cylinder and/or may be pushed out by screwing the stick according to viscosity of the paste. The composite material preserving container may be an electric cylindrical container or a desktop cylindrical container.

The filling method from the composite material preserving container to the small quantity preserving container may be by the existing method.

The composite material may be filled by a filling machine that may be a filling machine that is known in the art.

The following describes an example of a filling machine.

The filling machine comprises a feeder into which a composite material is charged, and a nozzle that discharges a composite material. A composite material charged into the feeder is discharged from the nozzle to be filled in the small quantity preserving container. A piston mechanism or a screw feeder may be used as the feeder.

In charging the composite material preserved in the composite material preserving container into the filling machine, a plurality of composite materials preserved in the composite material preserving container are charged into the filling machine. Therefore, air bubble mixing into a conventional composite material are observed. It was found that the air bubbles may be reduced and/or prevented by the composite material described herein, that may be formed using the composite material preserving step and the small quantity preserving container preserving step described above.

The composite material may be heated during filling, preferably may be heated to 15-45° C.

The small quantity preserving step includes a step of preserving the composite material filled in the composite material filling step in the small quantity preserving container for a pre-determined period.

The preservation temperature of the small quantity preserving container is at 1-40° C., and is preferably at 1-25° C. in a dark and cool place. The preserving period of the small quantity preserving container is for 50 days-5 years, is preferably 100 days-3 years.

The composite material is stabilized by preservation to obtain the composite material that is a uniform and has a stable pasty property. When a preservation period is over five years, deterioration of the composite material occurs and the pasty property of the composite material is in a non-uniform state. When a preservation period is within five years, deterioration of the composite material is not observed and obtains the composite material that is a uniform and has a stable pasty property.

The small quantity preserving container preserving step preferably includes a final evaluation step. The final product in a production process is inspected to confirm adaptability for shipping.

The final evaluation in the final evaluation step is a evaluation of the composite material performed in the small quantity preserving container preserving step. After the composite material filling step, an arbitrary small quantity preserving container among many small quantity preserving containers is evaluated.

In the composite material evaluation step, a differential scanning calorimetry (DSC) test, a hardening test, and/or a fluidity test or the like is preferably performed. Each test is performed by a measurement method known in the art to determine the acceptance or rejection. Acceptance or rejection is determined based on whether the test result is within a predetermined range. Although the predetermined range is important for determining the stability of the composite material, the predetermined range is widely changed depending on the species of the composite material etc. A detailed test method of a hardening test, and a fluidity (flow) test will be described in "characteristic confirmation test method" below.

The composite material may be shipped in the small quantity preserving container to be used by dentists and dental technicians that are the user of the composite material.

A characteristic confirmation test method for confirming an effect of the the composite material is described below. Also specific test methods of testing items of a mixed polymerizable monomer evaluating item and a composite material evaluating item is described below.

Viscous test: This test is also a mixed polymerizable monomer evaluating item

The mixed polymerizable monomer of 250 g was charged in a brown glass container and was left in a constant temperature room of 23+−1° C. for 24 hours. Then a viscosity value of the mixed polymerizable monomer is measured by using B type viscometer (BL type No. 3 rotor) after 5 minutes. A viscosity value of 5000-10000 mPa·S is necessary, and it is preferable to be viscosity value of 7000-9000 mPa·S. If the viscosity value is within the above ranges, good paste may be obtained.

Evaluation Criteria:
A: sufficiently mixed and no unevenness
B: insufficiently mixed and generating dissolution Hardening test: This test is also a mixed polymerizable monomer evaluating item and a composite material evaluating item A mixed polymerizable monomer or a composite material is filled in a metal mold with a hole having a thickness of 2 mm and diameter of 15 mm. A surface of the filled mixed polymerizable monomer or composite material is pressed into contact with a transparent plate glass and cured by an optional polymerization method. For example, the filled mixed polymerizable monomer or the filled composite material in the metal mold was exposed to light for 180 seconds using SOLIDILIGHT II (Shofu Inc.) to be cured. The Vickers hardness (kgf/mm$^2$) of the cured products was measured by the following measuring method.

The transparent plate glass being pressed into contact with the filled mixed polymerizable monomer or composite material was removed. The Vickers hardness on the surface of the cured products, which was pressed into contact with a transparent plate glass, was measured using a micro hardness tester (made by Akashi Seisakusyo K.K., merchandise code: "MVK-E") in 200 g load for 10 seconds. Measurement is performed 3 times in different positions and the average value of the 3 measurement times is defined as the Vickers hardness of the cured products.

Transmittance

The hardened material was prepared by the same preparation method as hardening test. Transmittance of the hardened material was measured in the wavelength range between 780 nm and 380 nm by means of spectrophotometer U-3200 (made by Hitachi Seisakusyo K.K.). Transmissivity of more than 95% is necessary, and it is preferable to be transmissivity of more than 99%.

Property/Visual Test

The composite material preserved in the composite material preserving container was taken out at a surface of the composite material and an inner portion of the composite material in composite material preserving container, and was scratched with a resinous spatula. Each of five dental technicians confirmed match state of the surface. The most frequent grade was set as the result of evaluation.

Evaluation Criteria:
A: Scratched portion of surface composite material with a resinous spatula showed luster. The silanated filler matched with a polymerizable monomer well at the scratched portion of surface composite material. Scratched portion of inner composite material with a resinous spatula showed luster. The silanated filler matched with a polymerizable monomer well at inner scratched portion.
B: Scratched portion of surface composite material with a resinous spatula showed slight luster. The silanated filler matched with a polymerizable monomer at the scratched portion of surface composite material. Scratched portion of the inner composite material with a resinous spatula showed luster. The silanated filler matched with a polymerizable monomer at inner scratched portion.
C: Scratched portion of surface composite material with a resinous spatula became slight white. The silanated filler matched with a polymerizable monomer at the scratched portion of surface composite material. Scratched portion of inner composite material with a resinous spatula showed luster. The silanated filler matched with a polymerizable monomer well at inner scratched portion. The property is different between the surface sample and the inner sample.
D: Scratched portion of surface composite material with a resinous spatula became white. The silanated filler did not match with a polymerizable monomer at the scratched portion of surface composite material. Scratched portion of inner composite material with a resinous spatula showed slight luster. The silanated filler matched with a polymerizable monomer at inner scratched portion. The property is completely different between the surface and the inner sample.

Small Amount Property/Visual Test

All composite material preserved in the small amount preserving container for 120 days are forced out. The composite material was scratched with a resinous spatula. Each of five dental technicians confirmed match state of the surface. The most frequent grade was set as the result of evaluation.

Evaluation Criteria:
A: Scratched portion of composite material with a resinous spatula showed luster. The silanated filler matched with the polymerizable monomer well at the scratched portion.
B: Scratched portion of composite material with a resinous spatula showed slight luster. The silanated filler matched with a polymerizable monomer at the scratched portion.
C: Scratched portion of composite material with a resinous spatula became slight white. The silanated filler matched with a polymerizable monomer at the scratched portion.
D: Scratched portion of composite material with a resinous spatula became white. The silanated filler did not match with a polymerizable monomer at the scratched portion of surface composite material.

Evaluation of Property Variation Between Lots

Twenty composite materials preserved in small quantity preserving containers for 120 days were prepared. The same test as the small amount property/visual test described above is performed to evaluate a property variation.

The results of this evaluation show a comparison with extruded composite material with regard to the property/visual test. Therefore, it is a prerequisite that the results of this evaluation is within the result of the small amount property/visual test. The evaluations show whether the property is sensuously different between the small quantity preserving containers within the result of the small amount property/visual test.

More specifically, for example, when evaluation criteria of the small amount property/visual test is "A: Scratched portion of composite material with a resinous spatula showed luster. The silanated filler matched with a polymerizable monomer well at the scratched portion," it is a prerequisite that all evaluation criteria of the 20 small quantity preserving containers is "A," and the evaluations show whether a sensuously difference of the property is observed between 20 small quantity preserving containers.

Evaluation Criteria:
A: Observed no variation in all of 20 small quantity preserving container.
B: Observed variation in five or less small quantity preserving container among 20 small quantity preserving container C: Observed variation in six or more small quantity preserving container among 20 small quantity preserving container Evaluation of Property Variation in Syringe One small quantity preserving container preserved for 120 days was prepared. All composite material preserved in the small amount preserving container was forced out and was divided into 4 parts.

The same test as the small amount property/visual test described above is performed to evaluate a property variation.

The results of this evaluation show a comparison with extruded composite material with regard to the property/visual test. Therefore, it is a prerequisite that the results of this evaluation is within the result of the small amount property/visual test. The evaluations show whether the property is sensuously different in the small quantity preserving container within the result of the small amount property/visual test.

Evaluation Criteria:
A: Observe no variation
B: Observe substantially no variation
C: Observe variation Bubbles Mixing Test One small quantity preserving container preserved for 120 days was prepared. All composite material preserved in the small amount preserving container is forced out. Then the composite material was exposed to light for 180 seconds using SOLIDILIGHT II (Shofu Inc.), and was cut every 1 millimeter to confirm presence of bubbles.

Evaluation Criteria:
A: No bubbles were observed
B: Small bubbles were observed without problem in use
C: Big bubbles were observed with problem in use Fluidity Test: This test is a mixed polymerizable monomer evaluating item and a composite material evaluating item The composite material of 0.5 ml is placed on a glass plate. Another one of a glass plate that is the same as the above is placed on the composite material. A weight is placed on the glass plate. The total weight of the weight and the glass plate where the weight is placed is 400 g. Ten minutes after placing the weight, the weight is removed. The composite material was exposed to light for 180 seconds using SOLIDILIGHT II (Shofu Inc.). Image analysis was performed by a personal computer to compute the spread area ($mm^2$). The obtained spread area is the flow value. A larger flow value indicates that the fluidity is superior. This test is performed ten times to calculate a standard deviation ($mm^2$) of ten test samples.

Intermittency Extrusion Test

The composite material was gathered by 0.5 ml once in 24 hours. After that without delay, a fluidity test was performed to evaluate a variation of the numerical value of the fluidity of the composite material gathered once in 24 hours.

Evaluation Criteria:
A: a variation of the numerical value is small (less than 1 mm)
B: a variation of the numerical value is large (1 mm or more)
C: incapable of pushing out on the way.

EXAMPLES

The following shows the names and abbreviations of the components used in the examples and the comparative examples.

Polymerizable Monomer
Bis-GMA: 2,2-bis(4-(3-(meth)acryloyloxy-2-hydroxypropoxy)phenyl)propane, 60 pts. wt.
UDMA: di(methacryloxyethyl)trimethylhexamethylenediurethan, 70 pts. wt.
TEGDM: triethyleneglycol-dimethacrylate, 30 pts. wt.
3G: triethyleneglycol(meth)acrylate, 40 pts. wt.
HEMA: 2-hydroxyethyl methacrylate,
Polymerizable Monomer Bearing Phosphate Ester Group
2-MEP: 2-(methacryloxy)ethyl phosphate
Bis-MEP: bis[2-(methacryloyloxy)-ethyl]phosphate
6-MHPA: 6-(methacryloxy)hexyl phosphonoacetate
Polymerizable Monomer bearing Dibasic Acid Carboxyl Group
4-AET: 4-Acryloxyethyltrimellitic acid
4-MET: 4-Methacryloxyethyltrimellitic acid
Filler
ASG filler: Aluminosilicate glass filler (average particle diameter of 5 µm)
FASG filler: Fluoroaluminosilicate glass filler (average particle diameter of 1.8 µm)
Ultrafine Particle Filler
R-972
Polymerization Accelerator
BBA•.Na: a sodium salt of 5-n-butylbarbituric acid
EB: p-N,N-Ethyl-dimethylaminobenzoate 1 pts. wt.
OT: Dioctyltin dilaurate 2 pts. wt.
Polymerization Initiator
CQ: Camphorquinone
Polymerization Inhibitor
BHT: Butylated hydroxytoluene The composite materials were prepared from materials shown in FIG. 1, under the condition shown in FIG. 1. The details are below.

Preparing Mixed Polymerizable Monomer

The polymerizable monomer and the polymerization initiator shown in FIG. 1 were mixed by mixer (Aikosha Inc.: BM) which uses a blade for mixing or a tumbler mixer (Seiwa Giken Inc.: TM). FIG. 1 shows mixing periods and mixing temperatures.

Among the numerical value of components of polymerizable monomer shown in FIG. 1, the numerical value of polymerization inhibitor (BHT) shows the adding amount with respect to 100 pts.wt. total amount of components of polymerizable monomer other than polymerization inhibitor (i.e. polymerization inhibitor is an externally content).

Preserving Mixed Polymerizable Monomer

After mixing, mixed polymerizable monomer is filled in the mixed polymerizable monomer preserving container (the capacity is 10 liters) having shading rate of no less than 99.99% and being a bottle type container with a lid and is preserved at 23° C.

Evaluation Mixed Polymerizable Monomer

A fluidity test, a hardening test, and a transmittance measurement are performed with respect to the preserved mixed polymerizable monomer. The test results are shown in FIG. 1.

Silantion Method
Silane Treatment Liquid:
Silane treatment liquid a: 3% of γ-methacryloyloxypropyltrimethoxysilane as silane coupling agent, 77% of ethyl alcohol, and 20% of water.
Silane treatment liquid b: 30% of γ-methacryloyloxypropyltrimethoxysilane as silane coupling agent, 69% of ethyl alcohol, and 1% of water.

A filler of 10 kg was heated and treated with 10 kg of "silane treatment liquid a" or 2 kg of "silane treatment liquid b". The silane treatment liquids were sprayed and were mixed for about 90 minutes in a treatment container with string. FIG. 2 and FIG. 3 shows which mixing machine is used. After mixing, the silanated filler was aged at 50° C. for 40 hours. Then, the temperature was raised and kept at 120° C. Next, the silanated filler was cooled to obtain silanated filler aggregates. The aggregates were charged in a Henschel mixer and was crushed at 1800 rpm for 5 minutes to prepare silanated fillers "a" and "b," of which the surfaces are coated with a poly(organo) siloxane.

Silanted Preserving Method

The silanated fillers of which the surfaces are coated with a poly(organo) siloxane are preserved in a polyethylene bag in 25 kg units at 10-25° C. for the preserving period as shown in FIG. 1.

Preparing Composite Material

The silanated filler and mixed polymerizable monomer preserved as shown FIG. 1. were mixed in an amount as shown FIG. 2 and FIG. 3 by a kneader (Inoue Seisakusho Co., Ltd: ND) or a planetary mixer (Inoue Seisakusho Co., Ltd: PM). The mixed polymerizable monomer is charged first. The composite material is prepared by mixing under the conditions as shown FIG. 2 and FIG. 3.

Preserving Composite Material in Composite Material Preserving Container

The composite material is filled in the composite material preserving container (the capacity is 4 liters) having a shading rate of no less than 99.99% and being a tray type container with a lid and is preserved under the conditions as shown FIG. 2 and FIG. 3.

Evaluating Composite Material

A hardening test and a property/visual test are performed with respect to the preserved composite material. The test results are shown in FIG. 2 and FIG. 3.

Filling Composite Material into Small Amount Preserving Container

The composite material in the composite material preserving container is charged into a cylinder of a filling machine. The cylinder is set on the nozzle of the filling machine. Three grams of the composite material is filled in a cylinder, which is as small amount preserving container, by a piston mechanism of the filling machine. For more detail, all of the composite material in the cylinder of a filling machine is filled in the cylinders as small amount preserving container. After that, the composite material in another composite material preserving container is continuously filled in the cylinder of a filling machine to continue the filling to the cylinders as small amount preserving container thereby obtaining the 2000 cylinder, which is as small amount preserving container, filled with small amount composite material. The cylinders are attached with a stick, a nozzle, a cap or the like to complete filling to the small amount preserving container.

After filling to the small amount preserving container, small amount property/visual test, evaluation of property variation between lots, evaluation of property variation in syringe, bubbles mixing test, fluidity test, and intermittently extrusion test were performed.

The test results are shown in FIG. 2 and FIG. 3. In a paste prepared by the method described herein, a change in properties was not observed in 120 days to 3 years. A change in properties was somewhat observed, but the pasty property remained stable for 3 years-5 years. Within 60 days, a pasty property was not stable and a significant change is properties change was observed. After 5 years, a significant change in properties change was observed.

The mixing method described herein provides stability of the properties for 60 days-5 years, preferably for 120 days-3 years. FIG. 4 shows the difference of the fluidity test result during the small amount preserving between the acceleration at the present time and the last time. It is shown that the composite material described herein is stable. Regarding the "difference," the column "60 days after" shows the difference between immediately after filling and 60 days after filling, the column "120 days after" shows the difference between after 60 days and after 120 days, the column "3 years after" shows the difference between after 120 days and after 3 years, the column "5 years after" shows the difference between after 3 years and after 5 years, the column "6 years after" shows the difference between after 5 years and after 6 years. The differences of the composite materials described herein are within 100 mm$^2$ and keep a stable fluidity. The differences of the comparative composite materials are over 100 mm$^2$ and do not keep a stable fluidity.

Although the preceding description has been described herein with reference to particular methods, materials and embodiments, it is not intended to be limited to the particular methods, materials and embodiments disclosed herein; rather, it extends to all functionally equivalent methods, materials and uses, such as are within the scope of the claims.

The invention claimed is:

1. A method for manufacturing a composite material comprising a silanated filler, a polymerizable monomer, and a polymerization initiator, the method comprising, in order, a mixed polymerizable monomer preparing step, a mixed polymerizable monomer preserving step, a composite material preparing step, a composite material preserving step, a composite material filling step, and a small quantity preserving container preserving step, wherein:

the mixed polymerizable monomer preparing step comprises charging the polymerization initiator into the polymerizable monomer in a mixing container, and mixing the polymerizable monomer and the polymerization initiator at a mixing temperature of 1-60° C. for a mixing period of 1 minute-24 hours to prepare a mixed polymerizable monomer, the mixed polymerizable monomer preserving step comprises preserving 1-50 liters of the mixed polymerizable monomer prepared in the mixed polymerizable monomer preparing step at a preserving temperature of 1-23° C. for a preserving period of 10 days-1.5 years, the composite material preparing step comprises performing a kneading step and a defoaming step, wherein the kneading step comprises kneading the mixed polymerizable monomer and the silanated filler at a kneading temperature of 5-60° C. for a kneading period of 5-40 minutes after charging the silanated filler into the mixed polymerizable monomer, wherein a ratio of the silanated filler to the mixed polymerizable monomer is 0.1-9 parts by weight of the silanated filler to 1 part by weight of the mixed polymerizable monomer, and the defoaming step comprises defoaming the mixed polymerizable monomer and the silanated filler at 5-200 Torr for a defoaming period of 5-30 minutes to prepare a composite material, the composite material preserving step comprises preserving 1-8 liters of the composite material prepared in the composite material preparing step at a preserving temperature of 1-25° C. for a preserving period of 10 days-1.5 years, the composite material filling step comprises filling the composite material preserved in the composite material preserving step by extrusion from a nozzle of a filling machine into a small quantity preserving container having 1-50 cc of volume, and the small quantity preserving container preserving step comprises preserving the composite material filled in the composite material filling step in the small quantity preserving container at a preserving temperature of 1-40° C. for a preserving period of 50 days-5 years.

2. The method for manufacturing a composite material according to claim 1, wherein the method further comprises, between the mixed polymerizable monomer preserving step and the kneading step of the composite material preparing step, a particulate filler kneading step that comprises kneading the mixed polymerizable monomer and a particulate filler at a kneading temperature of 5-60° C. for a kneading period of 5-30 minutes after charging the particulate filler into the mixed polymerizable monomer, wherein a ratio of the particulate filler to the mixed polymerizable monomer is 0.01-0.2 parts by weight of the particulate filler to 1 part by weight of the mixed polymerizable monomer, and a particulate filler defoaming step after the particulate filler kneading step that comprises defoaming the mixed polymerizable monomer and the particulate filler at 5-200 Torr for a defoaming period of 5-30 minutes, wherein the mixture obtained from the particulate filler kneading step and the particulate filler defoaming step is utilized in the subsequent composite material preparing step, wherein the particulate filler is kneaded with the mixed polymerizable monomer and the silanated filler in the kneading step of the composite material preparing step, wherein the particulate filler is defoamed with the mixed polymerizable monomer and the silanated filler in the defoaming step of the composite material preparing step, and wherein the composite material prepared in the defoaming step of the composite material preparing step comprises the particulate filler, the silanated filler, the polymerizable monomer, and the polymerization initiator.

3. The method for manufacturing a composite material according to claim 1, wherein the mixed polymerizable monomer preserving step comprises a mixed polymerizable monomer evaluation step of evaluating a portion of the mixed polymerizable monomer.

4. The method for manufacturing a composite material according to claim 1, wherein the composite material preserving step comprises a composite material evaluation step of evaluating a portion of the composite material.

* * * * *